United States Patent [19]
Canale

[11] Patent Number: 5,820,791
[45] Date of Patent: Oct. 13, 1998

[54] FRAGRANCE DISPENSER FOR AIR TREATMENT APPARATUS

[76] Inventor: William P. Canale, 28 Hollow La., Queensbury, N.Y. 12804

[21] Appl. No.: 503,319

[22] Filed: Jul. 17, 1995

[51] Int. Cl.⁶ .................................................. B01F 3/04
[52] U.S. Cl. ............................ 261/30; 239/54; 55/279; 261/DIG. 65; 422/124
[58] Field of Search .................... 239/54, 60; 55/279; 261/DIG. 65, 30; 422/124

[56] References Cited

U.S. PATENT DOCUMENTS

| | | | |
|---|---|---|---|
| 2,979,268 | 4/1961 | Brun | 239/60 |
| 3,685,734 | 8/1972 | Paciorek et al. | 239/54 |
| 4,306,892 | 12/1981 | Atalla et al. | 55/279 |
| 4,387,849 | 6/1983 | Van Loveren et al. | 239/60 |
| 4,604,114 | 8/1986 | Ward | 239/60 |
| 4,802,626 | 2/1989 | Forbes et al. | 239/60 |
| 5,074,416 | 12/1991 | Hustad | 426/129 |
| 5,087,273 | 2/1992 | Ward | 55/279 |
| 5,282,571 | 2/1994 | Smith et al. | 239/54 |
| 5,415,675 | 5/1995 | Powers et al. | 55/279 |
| 5,422,078 | 6/1995 | Colon | 239/54 |
| 5,547,636 | 8/1996 | Vick et al. | 261/DIG. 65 |

FOREIGN PATENT DOCUMENTS 2825171  12/1979  Germany ................................. 55/279

*Primary Examiner*—Tim R. Miles
*Attorney, Agent, or Firm*—Thomas L. Adams

[57] ABSTRACT

An air freshening device used in conjunction with an air circulation system of a building for impregnating the air with an aromatic scent. The device comprises a combination integrally-mixed plastic and scent substance formed through a manufacturing process that produces a shape for the scent impregnating device which permits it to be removeably attached to an air filter.

14 Claims, 2 Drawing Sheets

FRAGRANCE DISPENSER FOR AIR TREATMENT APPARATUS

FIELD OF THE INVENTION

This invention relates to a device for a fragrance dispenser generally for use in an air treatment systems and particularly appropriate for use in conjunction with those air treatment systems for building interiors.

BACKGROUND OF THE INVENTION

In both residential and commercial structures, there has been an increasing demand for devices to filter and circulate the air. One particular application of this is bars and dance halls in which the smells of body odors and cigarette products co-mingle to form a particularly offensive odor which is difficult to disperse.

Prior attempts have been made to combat offensive odors and to alter interior odors of rooms and buildings. These prior endeavors, however, have presented a significant number of disadvantages. Paramount among these disadvantages is their relatively high cost of production. It should be realized that even a slight increase in the cost of manufacture can generate a disproportionately large increase in cost to the end-user. Thus, while previous filter-aromatic combinations may at first appear to be or to have been relatively inexpensive to produce, on closer inspection they actually show themselves not to be particularly cost efficient in light of recent and continuing technological developments.

It is well-known that advances in the field of production can significantly influence the realm of consumer goods retailing. The air filter industry, which sells its products sold through retail outlets, is no exception to this fact. Prior art within this field discloses delivery systems that are relatively far from the optimal delivery system. In terms of simplicity, economy and ease in production, the optimal delivery system would be one in which the dispensing system and the fragrance-releasing essential oil could be combined. For many years, however, standard manufacturing processes caused the essential oils which comprised fragrances to break down when heated to the gelling temperatures of the plastics which comprise the preferred dispensing system. This break-down resulted in such a change in the chemical properties of essential oils that they would no longer be useful for their intended purpose: the retention of their fragrance for release into the air. The optimal development is a mixture which permits the entire filter-and-scent product and attaching system to be formed integrally in one operation as one item.

Recent technological developments currently permit elements of an essential oil to be mixed with common injection-moldable plastic such as polyethylene thereby permitting the extrusion of a resin that is a combination essential oil and plastic. Nevertheless, no individual or organization within the filter-scent industry has developed any type of product that demonstrates the novel and unobvious combination between plastic and scent which takes advantage of the new technology. Moreover, no prior art discloses a device in which combines filter-and-scent products formed as one item.

For example, U.S. Pat. No. 5,087,273 to L. D. WARD discloses a system in which scented plastic beads are encased in a mesh envelope and then attached to a filter system using a common paper clip-like hooking means.

Yet another drawback to inventions of the prior art is the fact that they often require the user to purchase special filter-aromatic combinations in lieu of standard filter types commonly available in the marketplace. This drawback is compounded by the fact that prior art efforts to impregnate the air with a fragrance or otherwise treat air most often require a different device for each prospective application. Thus, separate devices must be obtained for home air conditioners, for cars, for office complexes, for furnace heaters, far kitchen exhaust hoods, etc.

U.S. Pat. No. 4,604,114 to R. WARD discloses a fragrant scented air filter particularly adapted for use in conjunction with interior building air conditioning systems. In this system at least two solid rods of fragrant scented materials are embedded in the pad of air permeable porous, fibrous filtering material.

U.S. Pat. No. 4,306,892 to ATALLA, discloses a packet having securing elements but which contains a freshening medium within it. The packet and the air freshening medium are not incombination.

It can be seen from the foregoing that the invention of this application provides a simple and effective means for freshening air within an air circulation system. The use of extruded plastic combined with a scented substance into an integral combination provides for greater longevity of an air freshening device. This results in reduced cost to the user, and a lessening of the need for maintenance of the air circulation system. In addition, the ease with which the scented plastic shape of one of the embodiments of the disclosure of this invention can be attached inside an air circulation system permits effortless adaptation to virtually any, if not all filtration systems. Moreover, there are few scent delivery methods or devices which afford easy and convenient portability while still providing sufficiently effective fragrance potency. Among this limited selection of delivery methods, none has heretofore shown itself to be as efficient as well as simply constructed, easily operated, easily installed and inexpensive to produce.

SUMMARY AND OBJECTS OF THE INVENTION

Generally, the present invention is a device which provides a novel and simplified means for imparting a fragrant scent into the air of the interior of a building structure.

An object of this invention is to provide a scented fragrance releasing device for freely dispensing a scented fragrance into the air at a generally constant, prolonged rate upon the scented substance's exposure to air during use.

Another object of this invention is to provide a scented fragrance releasing device which is non-toxic.

Still another object of the present invention to produce a device that does not need to be re-impregnated with scent since it can be manufactured and sold cheaply enough that it would be considered disposable.

Yet still another object of this invention is to provide a scented fragrance releasing device which is simple and inexpensive to manufacture, relatively small to transport, simple to use, relatively inexpensive and packaged in a vapor-barrier bag that substantially maintains the scent within until use is desired.

Figure 1:
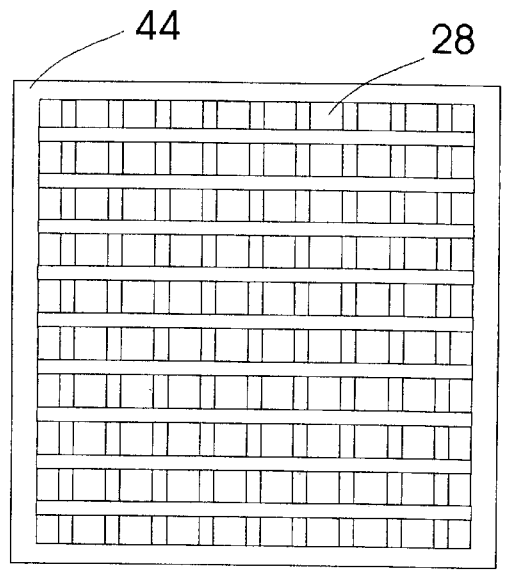
FIG. 1 is a front view of one embodiment.
Figure 2:
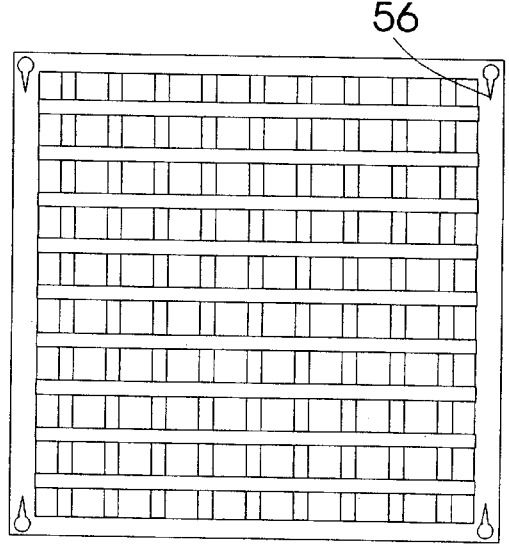
FIG. 2 is a rear view of the same embodiment shown in FIG. 1.
Figure 3:
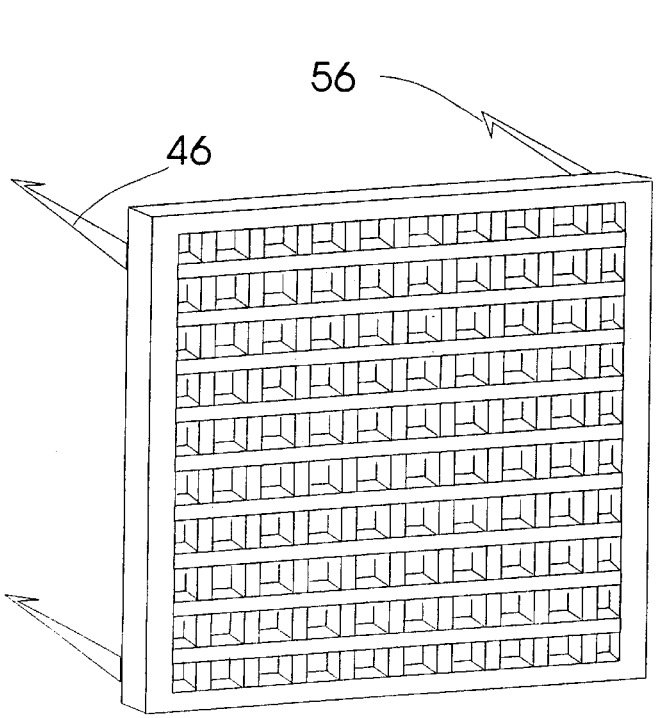
FIG. 3 is perspective view of FIG. 1.
Figure 4:
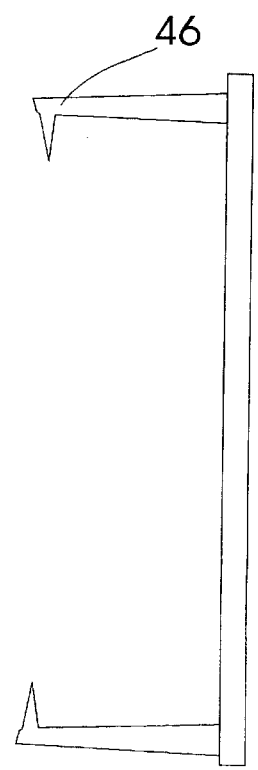
FIG. 4 is a side view of the embodiment shown in FIG. 1.
Figure 5:
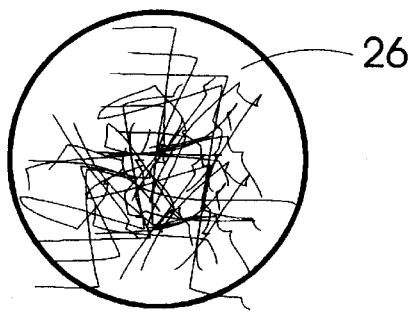
FIG. 5 is a view of conventional filter fibrous strands.
Figure 6:
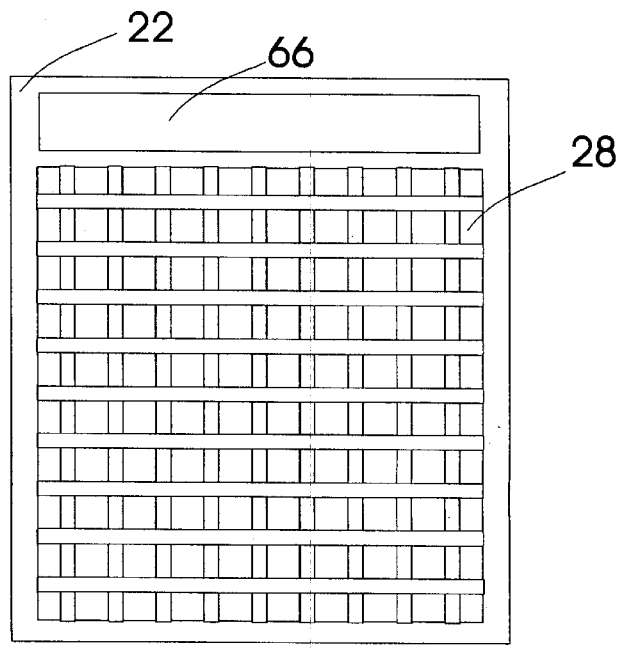
FIG. 6 is a rear view of an alternate embodiment in which attaching means to a conventional filter uses adhesive.
Figure 7:
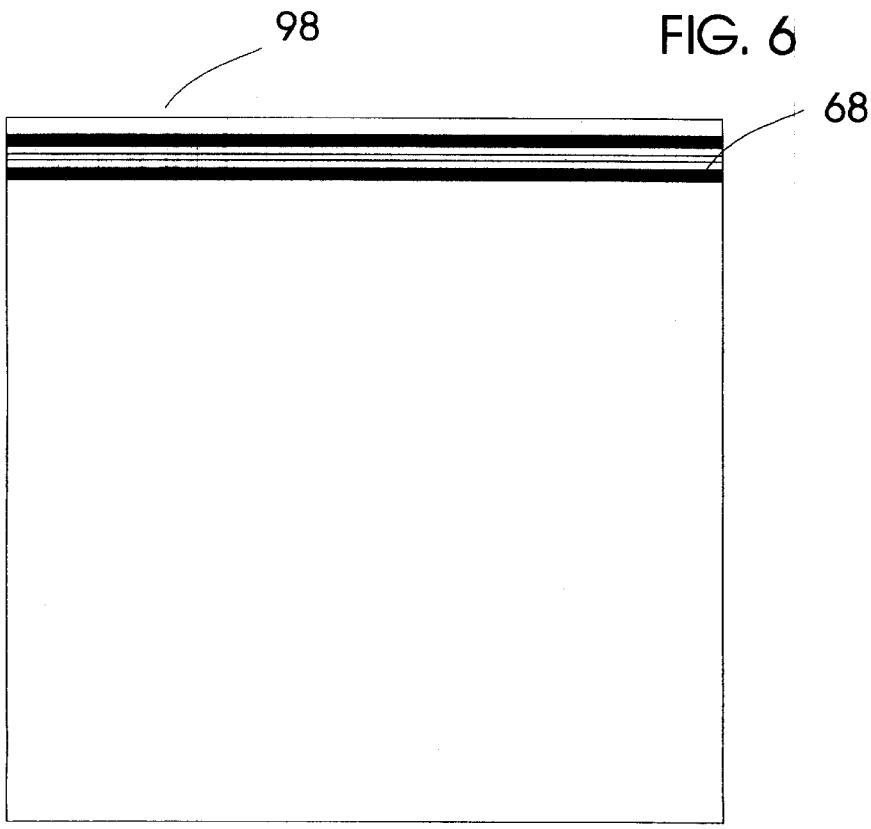
FIG. 7 shows a front view of a special re-sealable vapor-barrier bag.

26 fibrous strands
28 holes
44 sheet material
46 spoke
56 fish-hook-like tip
66 non-stick removable side
68 "zip-lock" fastening means
98 special bag

DESCRIPTION OF THE PREFERRED EMBODIMENT

Prior to extrusion using conventional plastic extrusion machinery, conventional pelletized chemical resin containing the essence of at least one essential oil is mixed together with standard plastic pellets. Generally, the preferred form of plastic is polyethylene. The combination batch is then fed into an extrusion machine at temperatures preferably between 278 degrees Fahrenheit, the flash point for melting conventional plastic, and 300 degrees Fahrenheit. Extruded preferably in sheet form, preferably approximately 1/30" of an inch in thickness, sheet material 44 is removed from the mold which made it. On at least one location on sheet material 44, at least one spoke 46 is preferably formed integral to sheet material 44 of a preferably cylindrical or triangular shape. The preferred number of spokes 46 is four (4) integrally formed into sheet material 44, preferably located one in each corner of sheet material 44 which is itself preferably formed in the shape of a square or square-approximating rectangle. Spoke 46 is preferably of a pre-determined length approximately 2/3 of an inch in thickness. On the tip of spoke 46 is formed a fish-hook-like tip 56. The function of fish-hook-like tip 56 is to permit the attachment of sheet material 44 to a conventional filter by means of tip 56 being inserted through the fibrous strands 26 comprising a conventional filter.

Sheet material 44 is preferably molded and preferably has geometrically-shaped holes 28 designed within such as square or circles or perhaps even some combination thereof, the purpose of which is to allow air to ventilate through sheet material 44 after sheet material 44 is attached to conventional filter 54 by means of fish-hook like tip 56. This method utilizes a protruding arrow formation which, as an attaching process simply pierces the relatively porous conventional filter in at least one part of its fibrous areas. In such a situation, however, sheet 44 is generally required to be injection-molded.

In an alternate embodiment, an alternate means to effect the adhesion of sheet material 44 to a conventional filter is effected by means of at least one pressure sensitive adhesive strip such as a common double sided-tape with its exterior, protective, non-stick and removable side 66 intact until use is desired. In this instance, when use is desired, non-stick and removable side 66 is pulled away and discarded, and then sheet material 44 is easily attached to a conventional filter. In an alternate embodiment, the attaching means to unite sheet material 44 with conventional filter 54 is integrally molded into sheet material 44.

In the instance that adhesive is inappropriate, a paper clip or other such attaching means may be employed by enjoining the fastening means through one of the holes in sheet 48 and then through the fibrous strands 26 offered by a conventional filter.

Regarding packaging, sheet material 44 is inserted into a special bag 98 preferably composed of a plastic polymer material such as EVOH™ which is extremely resistant to scent dissipation. The two ends of the bag are then sealed using a conventional heat-sealing machine. In a preferred embodiment, a co-mingling "zip-lock" fastening means 68 is preferably employed as a second-stage, re-sealing opening/closing means of special bag 98.

This invention is a novel combination and arrangement of elements. While preferred embodiments of the invention have been described using specific terms, such description is for illustrative purposes only. It may be appreciated that many changes and modification of the invention as described herein may be made by a person skilled in the art to which this subject matter pertains without substantially deviating from the spirit and scope of the invention and of the following claims. Consequently, it is not the intention of the applicant to limit his invention to those modes and embodiments of the invention shown or described above. All changes and modifications that come within the spirit of the invention are desired to be protected.

I claim:

1. For use in freshening air, the scent or fragrance releasing device for aroma enhancement in conjunction with an air filtration system, comprising:

a scent source means wherein said scent source means comprises material having an integral combination mixture of at least one scent and a plastic, said material having a reticulated plurality of apertures extending between opposite sides of said material to provide an airflow in a predetermined direction through said material along a straight path; and a fastening means mounted on and projecting from at least one location on said material for securing said scent source means to an air filter by reaching along said predetermined direction from one of the sides of said material directly to said air filter to grasp said air filter along said predetermined direction proximate the one location on said material.

2. The scent or fragrance releasing device of claim 1, wherein said material of said scent source means is sheet-like and has a pre-determined thickness.

3. The scent or fragrance releasing device of claim 1, wherein said fastening means comprises:

a spaced plurality of parallel spokes projecting from said material peripherally and being adapted to pierce and maintain contact with said air filter.

4. The scent or fragrance releasing device of claim 1, wherein said fastening means includes at least one integral protrusion of a pre-determined thickness;

an integral male-end suitable for piercing through and maintaining contact with the filtering material of said air filter.

5. The scent or fragrance releasing device of claim 1, wherein said fastening means includes a securable means which is removably securable.

6. The scent or fragrance releasing device of claim 1, including a package system comprising a sealable, odor-tight storage bag comprised of a polymer plastic for receiving said scent source means for ease in transport and handling and which further serves to prevent the substantial dissipation of said scent until use is desired.

7. The scent or fragrance releasing device of claim 6, wherein said package system is comprised of a vapor barrier plastic.

8. The scent or fragrance releasing device of claim 7, wherein said vapor barrier plastic comprises EVOH™.

9. The scent or fragrance releasing device of claim 6, wherein said package system has resealable closing means.

10. The scent or fragrance releasing device of claim 1, wherein said fastening means comprises:

at least one spoke projecting from said material and being adapted to pierce and maintain contact with said air filter.

11. The scent or fragrance releasing device of claim 10, wherein said spoke has a barbed tip.

12. The scent or fragrance releasing device of claim 10, wherein said spoke projects perpendicularly from a surface of said material.

13. The scent or fragrance releasing device of claim 1, wherein said fastening means comprises:

an adhesive mounted on said material to contact and adhere to said air filter.

14. The scent or fragrance releasing device of claim 13, wherein said adhesive comprises:

an adherent strip mounted on said material; and
a removable strip for detachably covering said adherent strip.

* * * * *